United States Patent [19]

Tuma et al.

[11] 3,934,003
[45] Jan. 20, 1976

[54] COSMETIC COMPOSITION CONTAINING AN ETHOXYLATED GLYCERIDE MIXTURE

[75] Inventors: Rudolf Tuma, Witten-Ruhr; Fritz Neuwald, Brammer ueber Nortorf, Holstein, both of Germany

[73] Assignee: Chemische Werke Witten GmbH, Germany

[22] Filed: Jan. 23, 1973

[21] Appl. No.: 326,077

Related U.S. Application Data

[63] Continuation of Ser. No. 645,618, June 13, 1967, abandoned, which is a continuation-in-part of Ser. No. 338,561, Jan. 20, 1964, abandoned.

[30] Foreign Application Priority Data

Apr. 13, 1963   Germany.............................. 29651

[52] U.S. Cl. ..................... 424/59; 424/70; 424/361
[51] Int. Cl.² ........................................... A61K 7/42
[58] Field of Search ................................. 424/59, 70

[56] References Cited

UNITED STATES PATENTS

| | | | |
|---|---|---|---|
| 2,615,159 | 10/1952 | Jackson ................................ | 424/70 |
| 2,875,128 | 2/1959 | Kirkpatrick ......................... | 424/170 |
| 2,976,251 | 3/1961 | Brokaw et al .................... | 424/284 X |
| 3,136,695 | 6/1964 | Tansey ............................ | 424/365 X |
| 3,192,057 | 6/1965 | Hines et al ..................... | 424/365 X |
| 3,192,193 | 6/1965 | Altscher et al. ................ | 424/365 X |
| 3,230,090 | 1/1966 | Weiss ................................ | 252/316 |
| 3,288,824 | 11/1966 | Mahler et al. ................... | 424/365 X |
| 3,330,731 | 7/1967 | Mehaffey ............................ | 424/78 |
| 3,335,053 | 8/1967 | Weitzel ............................ | 424/365 X |
| 3,341,465 | 9/1967 | Kaufman et al. ................ | 424/365 X |

OTHER PUBLICATIONS

Benton, American Perfumer and Cosmetics, Oct., 1963, Vol. 78, No. 10, pp. 37–40.

*Primary Examiner*—Dale R. Ore
*Attorney, Agent, or Firm*—Craig & Antonelli

[57] ABSTRACT

The present disclosure relates to a water-soluble and fat-restoring cosmetic and medicinal preparation comprising an ethoxylated glyceridic mixture of saturated vegetable fatty acids of about 8 to 14 carbon atoms, the glycerides of said acids having chemically linked thereto about 2 to 8 moles of ethylene oxide per free hydroxyl group. These substances may be admixed with other ingredients to form, for example, a hair tonic, an oil shampoo, a nutrient skin milk, a skin cream, a bath oil or sun tan oil. The ethoxylated mixture is preferably formed by reacting ethylene oxide at about 100°–150°C. with a glyceridic mixture having a fatty acid composition comprising caprylic acid, capric acid, lauric acid and myristic acid.

32 Claims, No Drawings

COSMETIC COMPOSITION CONTAINING AN ETHOXYLATED GLYCERIDE MIXTURE

The present application is a continuation of abandoned application Ser. No. 645,618 filed June 13, 1967, which application is a continuation-in-part of abandoned application Ser. No. 338,561, filed in the United States Patent Office on Jan. 20, 1964.

This invention relates to water-soluble and fat-restoring cosmetic and medicinal preparations which may be compounded in a variety of ways and used to treat the skin and the hair.

Cosmetic skin care has the object of preserving the normal condition of the skin and various preparations are known for this purpose. No sharp line of distinction can be drawn between cosmetic and medicinal preparations as they are interrelated in their functions. However, medicinal bath preparations are primarily intended to stimulate the metabolism of a diseased body by percutaneous action or to favorably influence the skin. Cosmetic bath preparations are, on the other hand, generally limited to the treatment of a healthy body and to the care of the body in a more restricted sense. The cosmetic bath additions, may, however, stimulate the entire metabolism and enhance a feeling of general well-being and either reduce or eliminate minor skin blemishes. Primarily, however, cosmetic bath additions are intended to assist or enhance the purifying effect of soap and water by softening the water and also to increase the appearance and feeling of good grooming by the application of ethereal oils and aromatic compounds. Such preparations are presently commercially available but it has been found that, as a result of the active substances and the surface-active purifying agents contained in such preparations, a defatting or degreasing of the skin surface sometimes occurs. These known preparations generally consist, at least partially, of materials which are active washing compounds and which frequently exhibit a fat-dissolving character because of their wetting effect.

In accordance with the present invention it has been found that cosmetic and medicinal preparations exhibit particularly favorable properties when substances are added thereto which, in addition to possessing a good water-solubility, cleansing action and purifying effect, also possess fat-restoring or regreasing properties. These substances are partial glyceride mixtures of saturated vegetable fatty acids having about 8 to 14 carbon atoms which have linked thereto, per hydroxyl group, 2 to 8 moles, preferably 4 to 8 moles, of ethylene oxide. Such substances are especially to be preferred which have 5 moles of ethylene oxide linked thereto per hydroxyl group.

The chemical characteristics of the partial glyceride mixtures employed in the present invention are as follows:

| | | |
|---|---|---|
| acid number | approx. | 1 |
| saponification number | | 250 |
| iodine number | less than | 1 |
| hydroxyl number | | 370 |
| monoester content | | 42% by weight |

Compositions having the foregoing characteristics and which also have 5 moles of ethylene oxide chemically linked thereto per hydroxyl group give the best results.

The condensation products used in the compositions according to the present invention are novel and may be prepared as described in the following.

Four moles (176.2 grams) of ethylene oxide is reacted at a temperature of 100°– 150°C. with one mole (232.5 grams) of a partial glyceride mixture having the following fatty acid composition:

| | |
|---|---|
| caprylic acid | 45 – 50% by weight |
| capric acid | 40 – 45% by weight |
| lauric acid | less than 8% by weight |
| myristic acid | less than 2% by weight |

This fatty acid composition is obtained by fractionating coconut oil fatty acid, which contains significant amounts of caprylic and capric acids. The above fatty acid composition itself has the following characteristics:

| | |
|---|---|
| acid number | 1 |
| saponification number | 245 |
| iodine number | 0.6 |
| hydroxyl number | 360 |
| monoester content | 43% by weight |

The ethoxylated reaction product obtained is soluble in water and may be used in various cosmetic preparations as the emollient component.

When condensing 5 moles of ethylene oxide with 1 mole of partial glyceride mixture, 220.3 grams of ethylene oxide is required. For the addition of 6 moles of ethylene oxide, 264.3 grams of ethylene oxide is necessary, and for the addition of 8 moles of ethylene oxide, 352.4 grams thereof is required.

All of the free hydroxyl groups in the glyceride mixture are ethoxylated when reacted with the ethylene oxide. The final products, as noted above, are water-soluble and, thus, do not form emulsions with water.

Many diversified preparations can be prepared which have, in addition to the desired purifying effect on the skin, a desired fat-restoring effect. About 10 to 50 percent by weight of such substances can be added to various cosmetic preparations, exemplary of which are skin milks, skin sprays, skin creams, as well as skin and hair shampoos. In the case of hair dressings or tonics, an addition of 2 to 10 percent by weight, preferably 5 percent by weight, has been found to be suitable.

Exemplary formulations in accordance with the present invention are further illustrated in the following specific examples, in which all percentages are by weight:

EXAMPLE I

Hair tonic with oil

| | |
|---|---|
| 1) isopropanol | 50% |
| 2) water | 45% |
| 3) partial glyceride mixture plus 4 moles of ethylene oxide per ho hydroxyl group | 5% |
| (Chemical characteristics of ethoxylated partial glyceride mixture: | |
| acid number | 0.2 |
| saponification number | 120 |
| hydroxyl number | 260). |

EXAMPLE II

Oil shampoo

| | |
|---|---|
| 1) triglyceride mixture of 8 to 12 carbon atoms | 5% |
| 2) partial glyceride mixture plus | |

EXAMPLE II
Oil shampoo

| | |
|---|---|
| 6 moles of ethylene oxide per hydroxyl group | 95% |
| (Chemical characteristics of ethoxylated partial glyceride mixture: | |
| acid number | 0.2 |
| saponification number | 89 |
| hydroxyl number | 180). |

EXAMPLE III
Nutrient skin milk

| | |
|---|---|
| 1) ethoxylated wool fat | 4% |
| 2) vitamin oil | 1% |
| 3) water | 80% |
| 4) partial glyceride mixture plus 4 moles of ethylene oxide per hydroxyl group | 15% |
| (Chemical characteristics of ethoxylated partial glyceride mixture: | |
| acid number | 0.2 |
| saponification number | 120 |
| hydroxyl number | 260). |

EXAMPLE IV
Skin cream with oil

| | |
|---|---|
| 1) triglyceride mixture (60% $C_R$ to $C_{12}$; 40% $C_{18}$) | 40% |
| 2) water | 30% |
| 3) partial glyceride mixture plus 4 moles of ethylene oxide per hydroxyl group | 30% |
| (Chemical characteristics of ethoxylated partial glyceride mixture: | |
| acid number | 0.2 |
| saponification number | 120 |
| hydroxyl number | 260). |

EXAMPLE V
Bath oil

| | |
|---|---|
| 1) pine needle oil | 29% |
| 2) 3',6-dihydroxyfluoran (fluorescin) | 1% |
| 3) partial glyceride mixture plus 5 moles of ethylene oxide per hydroxyl group | 70% |
| (Chemical characteristics of ethoxylated partial glyceride mixture: | |
| acid number | 0.1 |
| saponification number | 96 |
| hydroxyl number | 200). |

EXAMPLE VI
Sun tan oil

| | |
|---|---|
| 1) liquid paraffin | 5% |
| 2) dibenzalazine | 5% |
| 3) triglyceride mixture of 8 to 12 carbon atoms | 40% |
| 4) partial glyceride mixture plus 8 moles of ethylene per hydroxyl group | 50% |
| (Chemical characteristics of ethoxylated partial glyceride mixture: | |
| acid number | 0.1 |
| saponification number | 65 |
| hydroxyl number | 130) |

The expression "partial glyceride" in the present application is meant to refer to mixtures of mono- and diglycerides of the recited acids.

The invention being thus described, it will be obvious that the same may be varied in many ways. Such variations are not to be regarded as a departure from the spirit and scope of the invention and all such modifications are intended to be included within the scope of the following claims.

We claim:

1. A water-soluble and fat-restoring composition which consists of an ethoxylated glyceridic mixture of saturated vegetable fatty acids of about 8 to 14 carbon atoms, said mixture comprising the monoglycerides and diglycerides of said acids having chemically linked thereto about 2 to 8 moles of ethylene oxide per free hydroxyl group, said ethoxylated glyceridic mixture having an acid number of from 0.1 to 0.2, a saponification number of from 65 to 120 and a hydroxyl number of from 130 to 260.

2. A water-soluble and fat-restoring composition according to claim 1, wherein said fatty acids comprise a mixture of 45 to 50% by weight caprylic acid, 40 to 45% by weight capric acid, less than 8% by weight lauric acid, and less than 2% by weight myristic acid.

3. A water-soluble and fat-restoring composition according to claim 1, wherein said glyceridic mixture has chemically linked thereto about 4 to 8 moles of ethylene oxide per free hydroxyl group.

4. A cosmetic composition which consists of a cosmetic and a water-soluble and fat-restoring ethoxylated glyceridic mixture of saturated vegetable fatty acids of about 8 to 14 carbon atoms, said mixture comprising the monoglycerides and diglycerides of said acids having chemically linked thereto about 2 to 8 moles of ethylene oxide per free hydroxyl group, said ethoxylated glyceridic mixture having an acid number of from 0.1 to 0.2, a saponification number of from 65 to 120 and a hydroxyl number of from 130 to 260.

5. A cosmetic composition according to claim 4, wherein the cosmetic is hair tonic and said glyceridic mixture has chemically linked thereto about 4 moles of ethylene oxide per free hydroxyl group, said hair tonic consisting essentially of isopropanol and water.

6. A cosmetic composition according to claim 4, wherein the cosmetic is oil shampoo and said glyceridic mixture has chemically linked thereto about 6 mols of ethylene oxide per free hydroxyl group, said oil shampoo consisting essentially of a triglyceride mixture of fatty acids of 8 to 12 carbon atoms.

7. A cosmetic composition according to claim 4, wherein the cosmetic is nutrient skin milk and said glyceridic mixture has chemically linked thereto about 4 moles of ethylene oxide per free hydroxyl group, said nutrient skin milk consisting essentially of ethoxylated wool fat, vitamin oil and water.

8. A cosmetic composition according to claim 4, wherein the cosmetic is skin cream and said glyceridic mixture has chemically linked thereto about 4 mols of ethylene oxide per free hydroxyl group, said skin cream consisting essentially of a triglyceride mixture of fatty acids, 60% of which have 8 to 12 carbon atoms and 40% of which have 18 carbon atoms and water.

9. A cosmetic composition according to claim 4, wherein the cosmetic is bath oil and said glyceridic mixture has chemically linked thereto about 5 mols of ethylene oxide per free hydroxyl group, said bath oil consisting essentially of pine needle oil and 3',6-dihydroxyfluoran.

10. A cosmetic composition according to claim 4, wherein the cosmetic is sun tan oil and said glyceridic mixture has chemically linked thereto about 8 mols of ethylene oxide per free hydroxyl group, said sun tan oil consisting essentially of a triglyceride mixture of fatty acids of 8 to 12 carbon atoms, liquid paraffin and dibenzalazine.

11. A cosmetic composition according to claim 4, wherein from about 10 to 50% by weight of said ethoxylated glyceride mixture is added to said cosmetic when said cosmetic is a skin milk, a skin spray, a skin cream, a skin shampoo, or a hair shampoo, and from about 2 to 10% by weight of said ethoxylated glyceride mixture is added to said cosmetic when said cosmetic is a hair dressing or hair tonic.

12. A cosmetic composition which consists of a cosmetic and a water-soluble and fat-restoring ethoxylated glyceridic mixture comprising the monoglycerides and diglycerides of from 45 to 50% by weight caprylic acid, from 40 to 45% by weight capric acid, less than 8% by weight lauric acid and less than 2% by weight myristic acid, said monoglycerides and diglycerides having chemically linked thereto about 2 to 8 mols of ethylene oxide per free hydroxyl group, said ethoxylated glyceridic mixture having an acid number of from 0.1 to 0.2, a saponification number of from 65 to 120 and a hydroxyl number of from 130 to 260.

13. A cosmetic composition according to claim 12, wherein said monoglycerides and diglycerides have chemically linked thereto from 4 to 8 mols of ethylene oxide per free hydroxyl group.

14. A process for treating the hair which comprises applying thereto a hair dressing consisting essentially of an ethoxylated glyceridic mixture of saturated vegetable fatty acids of about 8 to 14 carbon atoms, said mixture comprising the monoglycerides and diglycerides of said acids, having chemically linked thereto about 4 mols of ethylene oxide per free hydroxyl group, in admixture with isopropanol and water.

15. A process for treating the hair according to claim 14, wherein said fatty acids comprise a mixture of 45 to 50% by weight caprylic acid, 40 to 50% by weight capric acid, less than 8% by weight lauric acid, and less than 2% by weight myristic acid.

16. A process for treating the hair according to claim 15, wherein said hair dressing contains from about 2 to 10% by weight of said ethoxylated glyceridic mixture.

17. A process for treating the hair which comprises applying thereto an oil shampoo consisting essentially of an ethoxylated glyceridic mixture of saturated vegetable fatty acids of about 8 to 14 carbon atoms, said mixture comprising the monoglycerides and diglycerides of said acids, having chemically linked thereto about 6 mols of ethylene oxide per free hydroxyl group, in admixture with a triglyceride mixture of fatty acids of 8 to 12 carbon atoms.

18. A process for treating the hair according to claim 17, wherein said fatty acids comprise a mixture of 45 to 50% by weight caprylic acid, 40 to 45% by weight capric acid, less than 8% by weight lauric acid, and less than 2% by weight myristic acid.

19. A process for treating the hair according to claim 18, wherein said oil shampoo contains from about 10 to 50% by weight of said ethoxylated glyceridic mixture.

20. A process for treating the hair according to claim 18, wherein said cosmetic composition contains from about 10 to 50% by weight of said ethoxylated glyceridic mixture.

21. A process for treating the skin which comprises applying thereto a cosmetic composition which consists of a cosmetic and a water-soluble and fat-restoring ethoxylated glyceridic mixture of saturated vegetable fatty acids of about 8 to 14 carbon atoms, said mixture comprising the monoglycerides and diglycerides of said acids, having chemically linked thereto about 2 to 8 mols of ethylene oxide per free hydroxyl group.

22. A process for treating the skin according to claim 21, wherein said cosmetic is a nutrient skin milk consisting essentially of ethoxylated wool fat, vitamin oil and water.

23. A process for treating the skin according to claim 21, wherein said cosmetic is a skin cream consisting essentially of a triglyceride mixture of fatty acids, 60 percent of which have 8 to 12 carbon atoms and 40 percent of which have about 18 carbon atoms.

24. A process for treating the skin according to claim 21, wherein said cosmetic is a bath oil consisting essentially of pine needle oil and 3',6-dihydroxyfluoran.

25. A process for treating the skin according to claim 21, wherein said cosmetic is a sun tan oil consisting essentially of a triglyceride mixture of fatty acids of 8 to 12 carbon atoms, liquid paraffin and dibenzalazine.

26. A process for treating the skin according to claim 21, wherein said fatty acids comprise a mixture of 45 to 50% by weight caprylic acid, 40 to 45% by weight capric acid, less than 8% by weight lauric acid, and less than 2% by weight myristic acid.

27. A hair tonic composition which consists essentially of about 50% isopropanol, about 45% water and about 5% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 4 mols of ethylene oxide per free hydroxyl group, said ethoxylated glyceridic mixture having an acid number of about 0.2, a saponification number of about 120 and a hydroxyl number of about 260.

28. An oil shampoo composition which consists essentially of about 5% of a triglyceride mixture of 8 to 12 carbon atoms and about 95% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 6 mols of ethylene oxide per free hydroxyl group, said ethoxylated glyceridic mixture having an acid number of about 0.2, a saponification number of about 89 and a hydroxyl number of about 180.

29. A nutrient skin milk composition consisting essentially of about 4% ethoxylated wool fat, about 1% vitamin oil, about 80% water and about 15% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 4 mols of ethylene oxide per free hydroxyl group, said ethoxylated glyceridic mixture having an acid number of about 0.2, a saponification number of about 120 and a hydroxyl number of about 260.

30. A skin cream composition which consists essentially of about 40% of a triglyceride mixture containing about 60% of triglycerides of fatty acids having from 8 to 12 carbon atoms and about 40% of triglyceride of fatty acids having 18 carbon atoms, about 30% water and about 30% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 4 mols of ethylene oxide per free hydroxyl group, said ethoxylated glyceridic mixture having an acid number of about 0.2, a saponification number of about 120 and a hydroxyl number of about 260.

31. A bath oil composition consisting essentially of about 29% pine needle oil, about 1% 3',6-dihydroxyfluoran and about 70% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 5 mols of ethylene oxide per free hydroxyl group, said ethoxylated glyceridic mixture having an acid number of about 0.1, a saponification number of about 96 and a hydroxyl number of about 200.

32. A sun tan oil composition consisting essentially of about 5% of liquid paraffin, about 5% of dibenzalazine, about 40% of triglyceride mixture of fatty acids having from 8 to 12 carbon atoms and about 50% of a water-soluble and fat-restoring ethoxylated glyceridic mixture of from 45 to 50% by weight caprylic acid, from 40 to 45% by weight capric acid, less than 8% by weight lauric acid and less than 2% by weight myristic acid, said ethoxylated glyceridic mixture comprising the monoglycerides and diglycerides of said acids having chemically linked thereto about 8 mols of ethylene oxide per free hydroxyl group, said ethoxylated glyceridic mixture having an acid number of about 0.1, a saponification number of about 65 and a hydroxyl number of about 130.

* * * * *